United States Patent [19]

Narayanan et al.

[11] Patent Number: 5,508,249
[45] Date of Patent: Apr. 16, 1996

[54] WETTING AGENT CONCENTRATE FOR AGRICULTURAL CHEMICALS

[75] Inventors: Kolazi S. Narayanan, Wayne; David W. Pritchard, Kinnelon, both of N.J.

[73] Assignee: ISP Investments Inc., Wilmington, Del.

[21] Appl. No.: 356,941

[22] Filed: Dec. 15, 1994

[51] Int. Cl.⁶ ..................................................... A01N 25/30
[52] U.S. Cl. .......................... 504/116; 504/213; 504/214; 514/788; 514/975; 71/DIG. 1
[58] Field of Search ..................................... 504/116, 213, 504/214; 71/DIG. 1; 514/788, 975

[56] References Cited

U.S. PATENT DOCUMENTS

| | | | |
|---|---|---|---|
| 4,695,465 | 9/1987 | Kigasawa et al. | 424/449 |
| 5,421,897 | 6/1995 | Grawe | 134/6 |
| 5,424,072 | 6/1995 | Narayanan et al. | 424/407 |

*Primary Examiner*—S. Mark Clardy
*Attorney, Agent, or Firm*—Joshua J. Ward; Marilyn J. Maue

[57] ABSTRACT

This invention relates to a stable wetting agent concentrate suitable for combination with an agrichemical which comprises a mixture of (a) a N—$C_8$ to $C_{18}$ alkyl lactam having from 4 to 6 carbon atoms in the heterocyclic ring and (b) a polyalkyleneoxide/polydimethyl siloxane copolymer, combined in a weight ratio of between about 10:90 and about 90:10 (a) to (b), and (c) between about 0.01 and about 25 wt.% based on total composition of an anionic surfactant, which composition exhibits synergistic wetting properties and allows for the use of lower effective dosages of the agrichemical due to induced cuticular and stomatical absorption by the plant species. The invention also pertains to the preparation of the wetting concentrate and its combination with an active component for use on a plant as a single phase composition.

13 Claims, No Drawings

WETTING AGENT CONCENTRATE FOR AGRICULTURAL CHEMICALS

BACKGROUND OF THE INVENTION

Wetting agents are an important part of agricultural chemical formulations, since they assure uniform distribution and efficient functioning of the active ingredient in a composition. For example, plant surfaces are typically hydrophobic and resist wetting by aqueous sprays, thereby reducing efficient deposition of the active chemical. Many different products are available for use as wetting agents including anionic, cationic, amphoteric and non-ionic types which suggest the wide chemical diversity and tendency for certain surfactant formulations to be optimum for certain active chemicals. In addition, specific interactions of various wetting agents with a specific active component can result in widely divergent responses so that selection of a highly effective wetting agent becomes difficult.

Selection of an appropriate and acceptable wetting agent often depends on the concentration of active material that the surfactant will accept and ecological limitations on the amount of active chemical that can be safely dispersed into the atmosphere. As a result of these considerations, certain active chemicals showing a degree of toxicity do not enjoy wide spread use since large amounts must be employed to effectively saturate the plant and undesirable amounts are dispersed to the atmosphere due to the inability of the wetting agent to retain a required dosage on the plant when using a normal volume of spray. Consequently, the search for economical wetting agents and their formulations, usable at low concentrations which provide enhanced agricultural chemical activity by improved wetting effectiveness, is ongoing.

Accordingly it is an object of this invention to provide an improved wetting agent composition which is a vehicle for the simultaneous cuticular and stomatic absorption of an agricultural chemical by a plant.

Another object of the invention is to provide a wetting agent having superior absorption capability by a plant which allows for the formulation of an effective agrichemical containing significantly lower dosages of the active chemical for treating plants.

Another object of the invention is to provide an economical and efficient wetting agent concentrate suitable for use with an agrichemical as a single phase aqueous solution.

These and other objects of the invention will become apparent form the following description and disclosure.

THE INVENTION

In accordance with this invention there is provided an improved water soluble concentrate having superior wetting properties for use in combination with an agriculturally active chemical or a formulation thereof. The present concentrate is an aqueous mixture of (a) a N—$C_8$ to $C_{18}$ alkyl lactam having from 4 to 6 carbon atoms in the heterocyclic ring and (b) a polyalkyleneoxide/polydimethylsiloxane copolymer having a number average molecular weight of from about 1,000 to about 1,000,000, combined in a weight ratio of between about 10:90 and about 90:10 (a) to (b) and (c) between about 0.01 and about 25 wt.% based on total composition of an anionic surfactant.

The above concentrate, containing between about 10 and about 50 wt.% water, preferably between about 20 and about 40 wt.% water, can be combined with a desired amount of active component in a solid or liquid state or the concentrate can be added to and mixed with the final formulation of the active component which has been diluted with water to a recommended concentration suitable for application to a plant. Addition of the concentrate to the final formulation suitable for spraying crops produces a single phase aqueous solution which eliminates nozzle clogging and problems associated with heterogeneous plant spray formulations, notably nonuniform distribution of the active component. Further, since the present wetting composition provides both cuticular and stomatal absorption by the plant and hence the active ingredient, somewhat lower dosages of the active component can be used to accomplish the desired result. This dual absorption feature is particularly beneficial when using ecologically objectionable herbicides whose toxicity prohibits high concentrations needed for efficacy in weed or crop spraying. A wide range of water soluble and water insoluble biologically active components are contemplated for use in the present invention, including pesticides, fungicides, herbicides, plant growth regulants, biocides, leaf defoliants and the like which may be in a liquid or finely divided granulated state. Examples of suitable active components include alpha-cyano-3-phenoxybenzyl-dichlorovinyl-2,2-dimethyl cyclopropane carboxylate, 3,6-dichloro-o-anisic acid, ethyl 2-[[[[(4-chloro-6-methoxy pyrimidin-2-yl) amino] carbonyl] amino] sulfonyl] benzoate (CLASSIC™), methyl 3-[[[[(4-methoxy-6-methyl-1,3,5-triazine-2-yl) amino]carbonyl] amino]sulfonyl]-2-thiophenecarboxylate (PINNACLE™), 5-ethyoxy-3-trichloromethyl-1,2,4-thiadiazole, tetramethyl thiuram disulfide, 0-ethyl-S,S-diphenyldithiophosphate, 0,0-dimethyl-0-(4-m-tolyl) phosphorothioate, (2-chloroethyl) phosphonic acid, 4-[(acetamino)methyl] -2-chloro-N(2,6-di-ethylphenyl acetamide, chloroethyl phosphonic acid and others named on pages 9–15 of copending patent application, Ser. No. 07/975,811, filed Nov. 13, 1992 by Kolazi Narayanan.

Component (a) in the above concentrate includes N— $C_8$ to $C_{18}$ alkyl pyrrolidones, N— $C_8$ to $C_{18}$ alkyl caprolactams and mono- or di- methyl substituted species of these lactams. The preferred lactams are the N— $C_8$ to $C_{12}$ alkyl pyrrolidones which may be employed individually or in admixture, particularly N— $C_8$ alone or mixtures of N— $C_8$ alkyl pyrrolidone with N— $C_{12}$ alkyl pyrrolidone. When lactam mixtures are employed, between about 10 and about 90 wt.% of either species can be employed; although mixtures containing 40 to 60 wt.% of one species is particularly recommended. AGROSOLVE®, supplied by International Specialty Products is a commercially available lactam mixture suitably employed in the present concentrate. When using a long chain lactam having more than 8 carbon atoms in the N-alkyl group, it is helpful to include a N— $C_1$ alkyl lactam, preferably N-methyl pyrrolidone, in the concentrate mixture to aide in solubilizing the higher lactam species. However, this solubilizer can be omitted, since after final dilution, i.e. the spray product, the higher lactams become soluble. When employed, the concentration of the N-methyl lactam can vary between about 0.1 and about 1.5 parts per part of total lactam.

The polyalkylene oxide/polydialkyl siloxane copolymer employed in the present concentrate generally contains between about 10 and about 80 wt.% polyalkylene oxide, preferably polyethyleneoxide and the copolymer more desirably has a number average molecular weight of between about 50,000 and about 100,000. Such copolymers are commercially available, e.g. as SILWET™ L77, L7001 and L7631, supplied by Union Carbide Corp.

The siloxane copolymers of the present invention are those containing units of

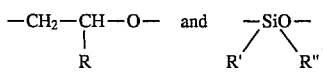

wherein R is hydrogen or $C_1$ to $_4$ alkyl, preferably methyl or ethyl; R' and R" are both lower alkyl. The most preferred copolymer is the polyethyleneoxide/polydimethylsiloxane in about 50:50 parts by weight ratio; although suitable weight ratios of lactam to siloxane copolymer can vary between about 10:90 and 90:10, more desirably between about 25:75 and about 75:25, a ratio of 45:55–55:45 is particularly recommended for good results.

As stated above, the concentrate also contains up to 25 wt.% of an anionic surfactant, more desirably 10–15 wt.%, based on the total composition. Suitable surfactants include sodium and potassium salts of sulfonates, sulfates, carboxylates, phosphates and phosphonates, ammonium or alkylammonium salts and alkanol ammonium salts.

Representative examples of suitable anionic surfactants are sodium dodecyl sulfate, alkoxylated $C_{10}$ to $C_{14}$ phosphate esters, $C_6$ to $C_{18}$ alkyl phosphates, sodium naphthalene sulfonate, lithium alkaryl sulfonates, sodium alkylbenzene sulfonates, alkyl tristyrylphosphate, sodium, potassium and ammonium triethanol amine salts of the above. Sodium $C_8$ to $C_{12}$ alkyl sulfates are particularly recommended for their high surfactant properties with respect to the lactam.

The concentrates of the present invention can be combined with the active component before or after formulation with other additives or before or after dilution of the formulation with water for use on plants. The final spray product formulation contains between about 0.05 and about 0.5 wt.%, preferably between about 0.1 and about 0.3 wt.% of the concentrate which is thoroughly mixed until a homogeneous, single phase aqueous solution is obtained.

The wetting compositions of the present invention are unique in that they possess synergistic properties which far exceed the beneficial effects achieved or expected with the higher alkyl pyrrolidones or the polyalkyleneoxide/polydimethylsiloxane copolymers alone. It is found that the mixture of these components performed unexpectedly better than the individual components at the same wetting agent concentration level, as shown below. More specifically, the wetting and spreading time of the aqueous formulations containing between about 0.05 and about 0.5 wt.%, preferably between about 0.1 and about 0.3 wt.%, of the present concentrate achieves a two to four fold reduction in wetting time over that obtained with similar formulations containing only the lactam or the copolymer. Further, the dual mode of plant uptake allows for more efficient use of the active component and permits a reduction in the amount needed to achieve desired results. Normally, between about 50–90% of a pesticidal or herbicidal spray is lost to the atmosphere, soil and ground water during commercial dusting or spraying. Use of the present concentrate solves this problem by effecting immediate dual absorption of the active chemical which is combined with the wetting agent in the composition. Hence, many of the effective pesticides and herbicides, which have been judged too toxic for general use in the treatment of plants, can now safely be made available. The long chain alkyl lactams of the present compositions are found to enhance the biological activity of the active component when the above concentration levels are maintained; whereas the silicone components, which have a low contact angle, promote the spreading of the bioactive compound and may be effectively incorporated at lower concentrations.

Having generally described the invention, reference is now had to the following examples which provide preferred and comparative examples; however, the examples are not to be construed as limiting to the scope of the present invention as set forth above and in the appended claims.

EXAMPLES 1–8

The following compositions were prepared. The components of Examples 3 and 4–8 were mixed in a glass beaker for 30 minutes at room temperature until a homogeneous liquid was obtained.

EXAMPLE 1

| Component | Percent Composition |
| --- | --- |
| N-Octylpyrrolidone | 0.0 |
| N-Methylpyrrolidone | 0.0 |
| N-Dodecylpyrrolidone | 0.0 |
| Na Lauryl $SO_4$ | 0.0 |
| Silwet L-77 | 100.0 |
| Water | 0.0 |
| Total | 100.0 |

EXAMPLE 2

| Component | Percent Composition |
| --- | --- |
| N-Octylpyrrolidone | 100.0 |
| N-Methylpyrrolidone | 0.0 |
| N-Dodecylpyrrolidone | 0.0 |
| Na Lauryl $SO_4$ | 0.0 |
| Silwet L-77 | 0.0 |
| Water | 0.0 |
| Total | 100.0 |

EXAMPLE 3

| Component | Percent Composition |
| --- | --- |
| N-Octylpyrrolidone | 50.0 |
| N-Methylpyrrolidone | 0.0 |
| N-Dodecylpyrrolidone | 0.0 |
| Na Lauryl $SO_4$ | 0.0 |
| Silwet L-77 | 50.0 |
| Water | 0.0 |
| Total | 100.0 |

EXAMPLE 4

| Component | Percent Composition |
| --- | --- |
| N-Octylpyrrolidone | 75.0 |
| N-Methylpyrrolidone | 0.0 |
| N-Dodecylpyrrolidone | 0.0 |
| Na Lauryl $SO_4$ | 0.0 |
| Silwet L-77 | 25.0 |
| Water | 0.0 |
| Total | 100.0 |

EXAMPLE 5

| Component | Percent Composition |
|---|---|
| N-Octylpyrrolidone | 53.7 |
| N-Methylpyrrolidone | 0.0 |
| N-Dodecylpyrrolidone | 0.0 |
| Na Lauryl SO$_4$ | 13.4 |
| Silwet L-77 | 0.0 |
| Water | 32.9 |
| Total | 100.0 |

EXAMPLE 6

| Component | Percent Composition |
|---|---|
| N-Octylpyrrolidone | 40.3 |
| N-Methylpyrrolidone | 0.0 |
| N-Dodecylpyrrolidone | 0.0 |
| Na Lauryl SO$_4$ | 13.4 |
| Silwet L-77 | 13.4 |
| Water | 32.9 |
| Total | 100.0 |

EXAMPLE 7

| Component | Percent Composition |
|---|---|
| N-Octylpyrrolidone | 20.2 |
| N-Methylpyrrolidone | 20.2 |
| N-Dodecylpyrrolidone | 13.2 |
| Na Lauryl SO$_4$ | 13.5 |
| Silwet L-77 | 0.0 |
| Water | 32.9 |
| Total | 100.0 |

EXAMPLE 8

| Component | Percent Composition |
|---|---|
| N-Octylpyrrolidone | 16.2 |
| N-Methylpyrrolidone | 16.2 |
| N-Dodecylpyrrolidone | 10.6 |
| Na Lauryl SO$_4$ | 10.8 |
| Silwet L-77 | 20.0 |
| Water | 26.4 |
| Total | 100.0 |

EXAMPLE 9

A modified Drave's wetting test*, was carried out on the compositions of each of the above examples after they had been diluted with water (reported in Table I) to simulate concentrations employed in commercial spray compositions.

*ASTM D 2281–68; 15.04, 1990

The wetting target was a 0.7 g. cotton skein and a 0.9 g. weight was suspended from the bottom of the cotton skein.

Comparisons were made between the present compositions, Examples 3–5 and 7) commercial wetting agents Silwet L-77 (Example 1) and N-octylpyrrolidone (Example 2) were made and wetting properties are shown in Table I.

The wetting times (Average time in seconds required to sink the cotton skein) are shown as a function of concentrations in Table I.

TABLE I

| | Sinking Time (seconds) | | Visual |
|---|---|---|---|
| % Conc. | Avg | SD | Appearance |
| Composition of Example 1 | | | |
| 0.503 | 3.6 | 0.6 | cloudy |
| 0.300 | 4.7 | 0.6 | cloudy |
| 0.250 | 5.5 | 0.4 | cloudy |
| 0.199 | 6.6 | 0.6 | cloudy |
| 0.145 | 8.2 | 0.9 | cloudy |
| 0.101 | 10.8 | 0.7 | hazy |
| 0.075 | 16.8 | 1.2 | hazy |
| 0.049 | 23.7 | 3.0 | hazy |
| Composition of Example 2 | | | |
| 0.500 | <1.5 | — | cloudy |
| 0.300 | <1.5 | — | cloudy |
| 0.250 | <1.5 | — | cloudy |
| 0.200 | <1.5 | — | cloudy |
| 0.150 | <1.5 | — | hazy |
| 0.102 | 5.5 | 0.7 | clear |
| 0.075 | 62.1 | 18.0 | clear |
| 0.052 | 714.4 | 174.8 | clear |
| Composition of Example 3 | | | |
| 0.500 | <1.5 | — | cloudy |
| 0.302 | <1.5 | — | cloudy |
| 0.253 | 2.7 | 0.2 | cloudy |
| 0.200 | 4.3 | 0.4 | cloudy |
| 0.151 | 6.1 | 0.6 | cloudy |
| 0.101 | 12.7 | 0.7 | hazy |
| 0.075 | 15.4 | 2.1 | hazy |
| 0.050 | 31.9 | 2.4 | slightly hazy |
| Composition of Example 4 | | | |
| 0.504 | <1.5 | — | cloudy |
| 0.301 | <1.5 | — | cloudy |
| 0.251 | <1.5 | — | cloudy |
| 0.201 | <1.5 | — | cloudy |
| 0.153 | <1.5 | — | hazy |
| 0.104 | 9.2 | 0.4 | clear |
| 0.076 | 22.6 | 1.7 | clear |
| 0.050 | 94.3 | 27.3 | clear |
| Composition of Example 5 | | | |
| 0.500 | <1.5 | — | clear |
| 0.300 | <1.5 | — | clear |
| 0.251 | <1.5 | — | clear |
| 0.200 | <1.5 | — | clear |
| 0.152 | 4.8 | 0.6 | clear |
| 0.103 | 9.0 | 0.6 | clear |
| 0.074 | 24.5 | 3.5 | clear |
| 0.049 | 702.3 | 354.9 | clear |
| Composition of Example 6 | | | |
| 0.500 | <1.5 | — | clear |
| 0.302 | <1.5 | — | clear |
| 0.252 | <1.5 | — | clear |
| 0.201 | 3.4 | 0.5 | clear |
| 0.152 | 5.8 | 0.5 | clear |
| 0.102 | 12.1 | 1.0 | clear |
| 0.075 | 24.3 | 4.2 | clear |
| 0.050 | 183.0 | 84.1 | clear |
| Composition of Example 7 | | | |
| 0.503 | <1.5 | — | clear |
| 0.300 | 3.0 | 0.4 | clear |
| 0.253 | 5.0 | 0.7 | clear |
| 0.200 | 6.6 | 0.8 | clear |
| 0.150 | 12.3 | 1.1 | clear |
| 0.100 | 24.2 | 3.5 | clear |

TABLE I-continued

| | Sinking Time (seconds) | | Visual |
|---|---|---|---|
| % Conc. | Avg | SD | Appearance |
| 0.075 | 54.0 | 10.0 | clear |
| 0.050 | 577.8 | 196.1 | clear |
| Composition of Example 8 | | | |
| 0.500 | <1.5 | — | clear |
| 0.300 | 3.2 | 0.6 | clear |
| 0.251 | 4.0 | 0.9 | clear |
| 0.200 | 6.3 | 0.3 | clear |
| 0.150 | 8.9 | 0.6 | clear |
| 0.101 | 19.0 | 1.7 | clear |
| 0.075 | 32.5 | 8.1 | clear |
| 0.051 | 77.1 | 21.3 | clear |

EXAMPLE 10

The following compositions shown in Table II were prepared as spray solutions and compared.

TABLE II

| Composition (a) Blank | |
|---|---|
| PINNACLE 25 DF | 0.25 oz. (7 g.) |
| CLASSIC 25 DF | 0.25 oz. (7 g.) |
| Water | 20 gallons |
| Composition (b) | |
| PINNACLE 25 DF | 0.25 oz (7 g.) |
| CLASSIC 15 DF | 0.25 oz (7 g.) |
| Concentrate of Example 6 | 75 g. |
| Water | 20 gallons |
| Composition (c) | |
| PINNACLE 25 DF | 0.25 oz (7 g.) |
| CLASSIC 24 DF | 0.25 oz (7 g.) |
| Concentrate of Example 6 | 150 g. |
| Water | 20 gallons |
| Composition (d) | |
| PINNACLE 25 DF | 0.25 oz (7 g.) |
| CLASSIC 25 DF | 0.25 oz (7 g.) |
| Concentrate of Example 6 | 375 g. |
| Water | 20 gallons |
| Composition (e) | |
| PINNACLE 25 DF | 0.25 oz (7 g.) |
| CLASSIC 25 DF | 0.25 oz (7 g.) |
| Concentrate of Example 5 | 75 g. |
| Water | 20 gallons |
| Composition (f) | |
| PINNACLE 25 DF | 0.25 oz (7 g.) |
| CLASSIC 25 DF | 0.25 oz (7 g.) |
| Concentrate of Example 5 | 150 g. |
| Water | 20 gallons |
| Composition (g) | |
| PINNACLE 25 DF | 0.25 oz (7 g.) |
| CLASSIC 25 DF | 0.25 oz (7 g.) |
| Concnetrate of Example 5 | 375 g. |
| Water | 20 gallons |
| Composition (h) | |
| PINNACLE 25 DF | 0.25 oz (7 g.) |
| CLASSIC 25 DF | 0.25 oz (7 g.) |
| SILWETT L 77 | 77 g. |
| Water | 20 gallons |
| Composition (i) | |
| PINNACLE 25 DF | 0.25 oz (7 g.) |
| CLASSIC 25 DF | 0.25 oz (7 g.) |
| SILWETT L 77 | 150 g. |

TABLE II-continued

| Water | 20 gallons |
|---|---|
| Composition (j) | |
| PINNACLE 25 DF | 0.25 oz (7 g.) |
| CLASSIC 25 DF | 0.25 oz (7 g.) |
| SILWETT L 77 | 375 g. |
| Water | 20 gallons |

EXAMPLE 11

The compositions prepared above in Table II were subjected to biological field tests during clear weather at 50% humidity, low wind velocity and 80° F. temperature. A sprayer equipped with a 10 inch nozzle Teejet tip operated at 35 psi pressure was operated at a rate of 20 gals/acre of herbicide. The plants tested, in a 45×10 foot plot, had about 5 inch growth. Three replicates of each plant was sprayed and, 18 days after spraying, the results were catagorized as to broadleaf* control and soybean injury. The results of these tests are reported in following Table III.

*camphor weed, jerusalem oak, lambsquarter, pigweed, spanish needles and teaweed.

TABLE III

| Spray Composition | % Broadleaf Control | % Soybean Injury |
|---|---|---|
| (a) | 50* | 3 |
| (b) | 65 | 0 |
| | 60 | 0 |
| | 80 | 5 |
| (c) | 70 | 5 |
| | 75 | 5 |
| | 75 | 5 |
| (d) | 80 | 10 |
| | 80 | 10 |
| | 95 | 5 |
| (e) | 70 | 5 |
| | 60 | 5 |
| | 40 | 0 |
| (f) | 72 | 5 |
| | 65 | 5 |
| | 70 | 5 |
| (g) | 70 | 5 |
| | 65 | 0 |
| | 65 | 5 |
| (h) | 60 | 8 |
| (i) | 66 | 10 |
| (j) | 77* | 15 |

*estimated value

What is claimed is:

1. An aqueous agricultural chemical solution containing between about 0.05 and about 1.0 weight % of a clear, homogeneous wetting agent concentrate consisting essentially of:

(a) a N— $C_8$ to $C_{18}$ alkyl lactam having from 4 to 6 carbon atoms in a heterocyclic ring;

(b) a polyalkyleneoxide/polydimethylsiloxane copolymer combined in a weight ratio of between about 10:90 and about 90:10 lactam (a) to copolymer (b) and (c) between about 0.01 and about 25 wt.% based on total composition of an anionic surfactant.

2. The concentrate of claim 1 wherein said copolymer is combined in a weight ratio of between about 25:75 and about 75:25.

3. The concentrate of claim 1 wherein said lactam is a N— $C_8$ to $C_{12}$ alkyl pyrrolidone.

4. The concentrate of claim 3 wherein said lactam is N— $C_8$ alkyl pyrrolidone.

5. The concentrate of claim 3 wherein said lactam is a mixture of a N—$C_8$ alkyl pyrrolidone and a N—$C_{12}$ alkyl pyrrolidone.

6. The concentrate of claim 1 wherein said copolymer has a number average molecular weight of from about 50,000 and about 100,000.

7. The concentrate of claim 1 wherein said anionic surfactant is an alkali metal salt of a $C_6$ to $C_{18}$ alkyl sulfate.

8. The concentrate of claim 7 wherein said surfactant is sodium lauryl sulfate.

9. The concentrate of claim 1 in admixture with an effective plant altering amount of an agriculturally active compound.

10. The solution of claim 1 wherein said aqueous solution is a water solution and the concentrate is present in water at a concentration of between about 0.1 and about 0.3 wt.%.

11. The concentrate of claim 1 wherein the lactam (a) component contains a N-alkyl group having more than 8 carbon atoms and wherein the concentrate contains between about 0.1 and about 1.5 parts of N-methyl lactam per part of total lactam.

12. The concentrate of claim 11 wherein the concentrate contains between about 0.3 and about 1 part of N-methyl lactam per part of total lactam.

13. The concentrate of claim 11 wherein (a) contains N-dodecyl pyrrolidone.

* * * * *